US010172995B2

United States Patent
Radwanski et al.

(10) Patent No.: US 10,172,995 B2
(45) Date of Patent: Jan. 8, 2019

(54) SYSTEM AND METHOD FOR DETERMINING IRRADIATION EXPOSURE TIME WITH IRRADIATION SENSORS DURING EXTRACORPOREAL PHOTOPHERESIS

(71) Applicant: Fenwal, Inc., Lake Zurich, IL (US)

(72) Inventors: Katherine N. Radwanski, Des Plaines, IL (US); Christopher J. Wegener, Libertyville, IL (US)

( * ) Notice: Subject to any disclaimer, the term of this patent is extended or adjusted under 35 U.S.C. 154(b) by 192 days.

(21) Appl. No.: 14/616,422

(22) Filed: Feb. 6, 2015

(65) Prior Publication Data

US 2015/0196706 A1    Jul. 16, 2015

Related U.S. Application Data (63) Continuation-in-part of application No. PCT/US2013/024893, filed on Feb. 6, 2013.

(51) Int. Cl.
*A61M 1/36* (2006.01)

(52) U.S. Cl.
CPC ........ *A61M 1/3683* (2014.02); *A61M 1/3607* (2014.02); *A61M 1/3686* (2014.02); *A61M 1/3692* (2014.02); *A61M 1/3696* (2014.02); *A61M 1/3693* (2013.01); *A61M 2205/3313* (2013.01)

(58) Field of Classification Search
CPC .............. A61M 1/3683; A61M 1/3607; A61M 1/3693; A61M 2205/3313; A61M 1/3696; A61M 1/3692

See application file for complete search history.

(56) References Cited

U.S. PATENT DOCUMENTS

| 5,360,542 A | 11/1994 | Williamson et al. |
| 6,027,657 A | 2/2000 | Min et al. |
| 6,219,584 B1 | 4/2001 | Lee |
| 6,277,337 B1 | 8/2001 | Goodrich, Jr. et al. |

(Continued)

FOREIGN PATENT DOCUMENTS

| DE | 42 35 841 A1 | 4/1994 |
| EP | 1 674 120 B1 | 6/2006 |
| EP | 1867355 A1 | 12/2007 |

(Continued)

OTHER PUBLICATIONS

The International Bureau of WIPO, International Preliminary Report on Patentability (Chapter I), dated Aug. 11, 2015.

(Continued)

*Primary Examiner* — Leslie Deak
(74) *Attorney, Agent, or Firm* — Hanna Yoon; Scott M. Day (57) ABSTRACT

An irradiation device for photopheresis, comprising an exposure chamber configured to receive an illumination container holding a target cell suspension; an irradiation source configured to irradiate the illumination container and target cell suspension for a certain exposure time period; an irradiation sensor configured to detect the intensity of irradiation emitted by the irradiation source; and a processing circuit coupled to the irradiation sensor and configured to treat the target cell suspension with a predetermined treatment dosage of radiation, wherein the processing circuit adjusts the exposure time period based on the intensity of irradiation in order to achieve the predetermined treatment dosage.

9 Claims, 9 Drawing Sheets

(56) References Cited

U.S. PATENT DOCUMENTS 7,433,030 B2 10/2008 Waldo et al.
2004/0186412 A1 9/2004 Mallett et al.

FOREIGN PATENT DOCUMENTS

| WO | WO/1997/36581 A1 | 10/1997 |
| WO | 2004033081 A2 | 4/2004 |
| WO | WO/2014/123521 A | 8/2014 |

OTHER PUBLICATIONS

International Searching Authority, International Search Report for PCT/US2013/024893, dated Aug. 8, 2014.
European Search Report for application No. 16154065.3, dated Jun. 22, 2016, 7 pages.
International Search Report for application No. PCT/US2013/024893, dated Apr. 7, 2014, 6 pages.
Written Opinion of the International Searching Authority for application No. PCT/US2013/024893, dated Apr. 7, 2014, 9 pages.
International Preliminary Report on Patentability for application No. PCT/US2013/024893, dated Aug. 11, 2015, 10 pages.
Communication Pursuant to Art. 94(3) EPC for application No. EP 16154065.3, dated Jun. 20, 2017, 4 pages.

SYSTEM AND METHOD FOR DETERMINING IRRADIATION EXPOSURE TIME WITH IRRADIATION SENSORS DURING EXTRACORPOREAL PHOTOPHERESIS

CROSS REFERENCE TO RELATED APPLICATIONS

This application is a continuation-in-part of International Application PCT/US13/24893, filed Feb. 6, 2013, the entire contents being incorporated herein by reference.

FIELD OF THE DISCLOSURE

The present disclosure is directed to a method for performing extracorporeal photopheresis of target cells and, more particularly, to a system and method of determining the appropriate irradiation exposure time to target cells during photopheresis treatment.

BACKGROUND

Light irradiation therapy is used for the treatment of various blood diseases to, e.g., eliminate immunogenicity in cells, inactivate or kill selected cells, inactivate viruses or bacteria, or activate desirable immune responses. For example, it is known to use the photoactivatable drug psoralen to treat pathogenic blood cells, such as lymphocytes, in an extracorporeal photopherisis (ECP) procedure in which the patient receives 8-methoxypsoralen (8-MOP), blood is withdrawn from the patient, the white cells separated (typically by centrifugation), and subjected to UV light to activate the 8-MOP molecules. The photoactivated 8-MOP alters the DNA of the pathogenic leukocytes, and the fluid with the altered leukocytes is reinfused back into the patient to induce an immune system response.

A difficulty in performing phototherapy is the delivery of the proper dose of light energy to the photoactivatable material in the suspension, particularly if the suspension includes material that is not substantially transparent to light so that it attenuates the light energy intended for photoactivation, or if the target cells are not uniformly distributed on the fluid surface, in which case target cells closest to the surface may serve to attenuate light energy with respect to those target cells beneath the surface.

A method for delivering a desired dose of light energy to a suspension is disclosed in U.S. Pat. No. 6,219,584, to Therakos, Inc. This patent is directed to an "online" photopheresis system that includes both the blood separation device and the photoactivation device in an integrated, closed system. In this and other Therakos systems, a complex algorithm is used to determine the emitted dose ("fluid light energy value" or FLEV) needed to achieve the target dose (the "target's effective light energy value" or TELEV) that is to be delivered to the targeted leukocytes (mononuclear cells or MNC). This algorithm requires knowledge of the thickness ratio of the product, as well as the light transmittance value of the product that is measured for every product using a hematocrit sensor.

In "offline" methods, (such as those practiced when using the phototherapy systems available from Macopharma SA or Vilber Lourmet), the UV dose is monitored by sensors which are angled to detect UV light emitted from the UV bulbs as well as that reflected from the mirrored surface behind each set of bulbs (and presumably less light is reflected back if the treated cell product is absorbing more light). This method does not fully account for the UV light being absorbed by the red cells and plasma, and operators are required to manually measure the product hematocrit and adjust it (if necessary) to lower than 2% because the UV dose delivered at higher hematocrits is unknown (and likely insufficient).

In accordance with the method described below, a dedicated hematocrit sensor is not required, but only moderate control of a preset product volume and hematocrit of the suspension to be treated is required. The desired light dose to be received by the target cells is determined based on the therapeutic response of the target cells, thus providing for a more precise therapeutic result than simply applying a correction factor to the emitted light dose. The desired light dose to be received by the target cells is also more accurately controlled by UV light sensors that account for variation in UV light emission.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

According to an exemplary embodiment, the present disclosure is directed to an irradiation device for photopheresis, comprising an exposure chamber configured to receive an illumination container holding a target cell suspension; an irradiation source configured to irradiate the illumination container and target cell suspension for a certain exposure time period; an irradiation sensor configured to detect the intensity of irradiation emitted by the irradiation source; and a processing circuit coupled to the irradiation sensor and configured to treat the target cell suspension with a predetermined treatment dosage of radiation, wherein the processing circuit adjusts the exposure time period based on the intensity of irradiation in order to achieve the predetermined treatment dosage.

According to an exemplary embodiment, the present disclosure is directed to a method for determining irradiation exposure time during an extracorporeal photopheresis procedure, comprising the steps of providing an exposure chamber configured to receive an illumination container holding a target cell suspension containing a selected amount of a photoactivation agent; providing an irradiation device having an irradiation source configured to irradiate contents within the illumination container and target cell suspension for a certain exposure time period; providing an irradiation sensor within the irradiation device configured to detect the intensity of irradiation emitted by the irradiation source; designating a treatment dosage value for emission by the irradiation source; detecting with the irradiation sensor the intensity of irradiation emitted by the irradiation source and determining a suitable irradiation exposure time period to achieve the designated treatment dosage; and irradiating the target cell suspension with the irradiation source for the exposure time period.

BRIEF DESCRIPTION OF THE DRAWINGS

Features, aspects, and advantages of the present embodiments will become apparent from the following description, appended claims, and the accompanying exemplary embodiments shown in the drawings, which are briefly described below.

DETAILED DESCRIPTION

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

Figure 1:
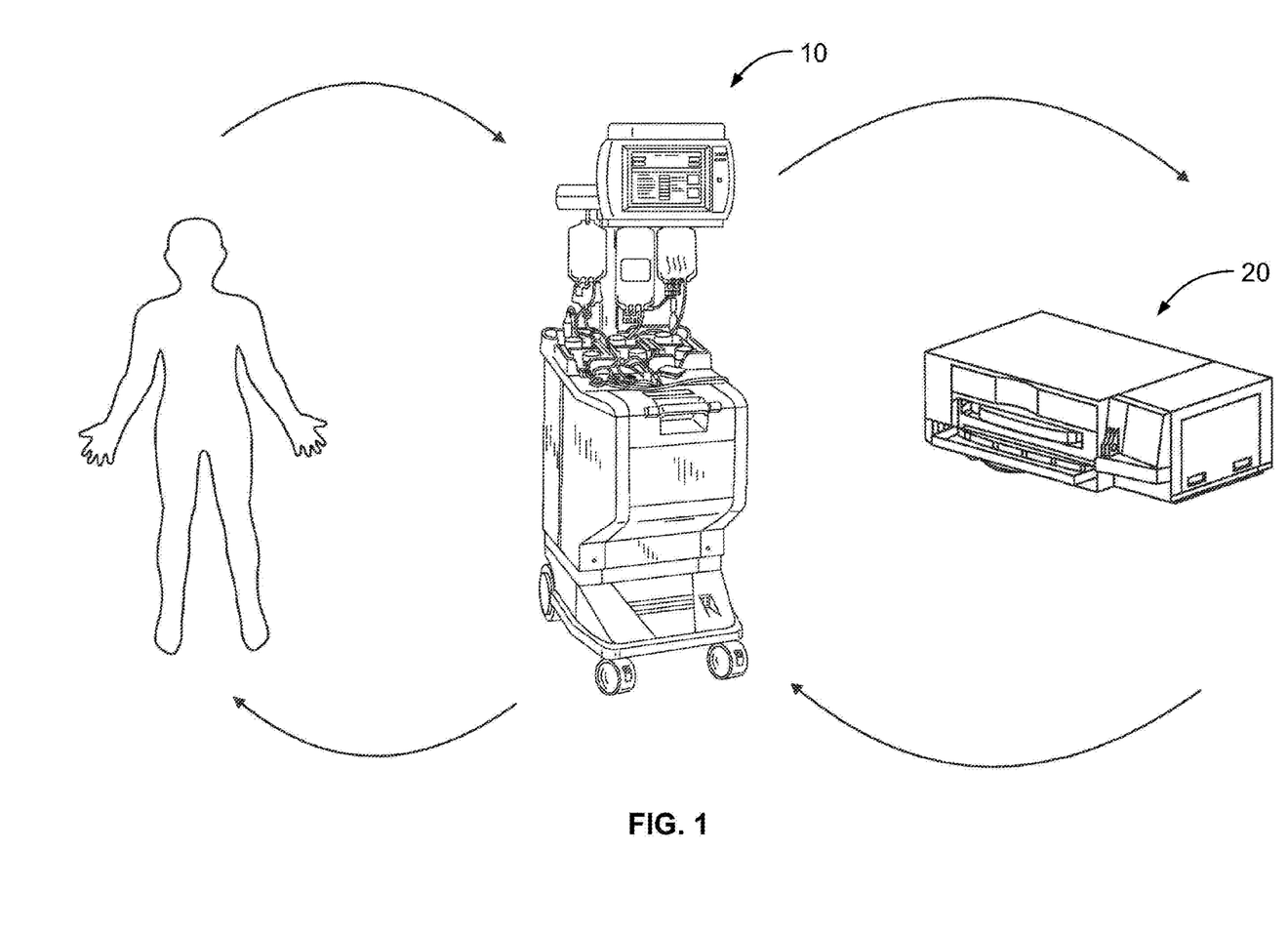
FIG. 1 is a diagram generally showing the mechanical components of a photopheresis treatment, according to an exemplary embodiment.

FIG. 1 shows, in general, the mechanical components that make up the system and that are used in the methods described herein. In accordance with the present disclosure, the system includes a separation component 10 and a treatment (i.e., irradiation) component 20. Preferably, irradiation component 20 is independent and housed separately from separation component 10. Although separately housed and independent devices, it is preferable that separation device 10 and irradiation device 20 are located adjacent to each other. While FIG. 1 shows a preferred embodiment of separated separation and irradiation components, it will be appreciated that the methods described herein may also be used with devices having integrated separation and irradiation components, such as the Therakos systems described above.

Figure 4:
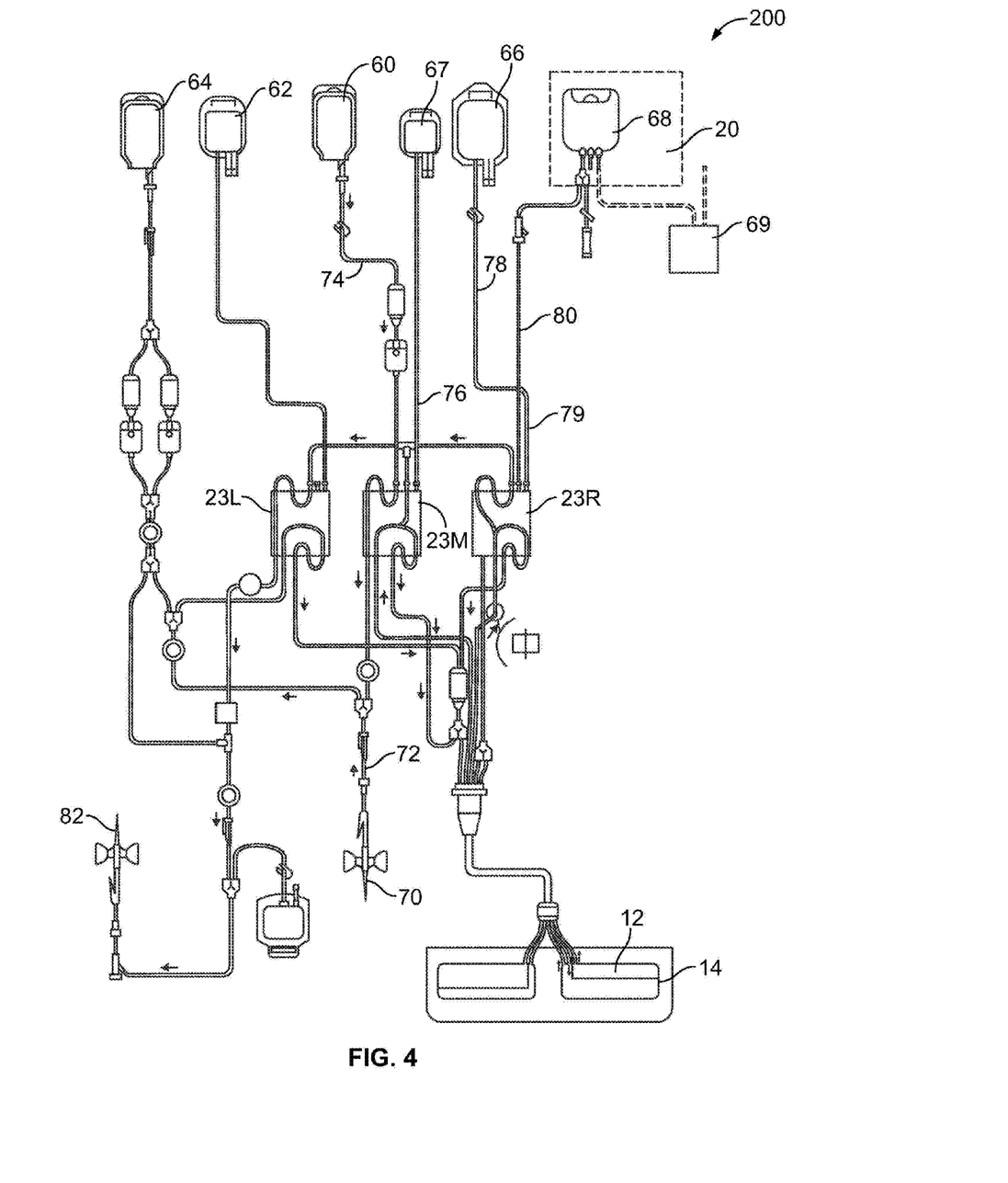
FIG. 4 is a diagram of the fluid circuit useful in the collection, treatment and reinfusion of the target cell population, according to an exemplary embodiment.

In accordance with the systems and methods described herein a patient is connected to a blood processing set, i.e., fluid circuit 200. As generally illustrated in FIGS. 1 and 4, fluid circuit 200 provides a sterile closed pathway between separation component 10 and irradiation component 20. The system described herein also optionally includes a washing component which, preferably, is housed within the separation component. Preferably, the separation component 10 and washing component are one and the same.

With reference to FIG. 1, whole blood is withdrawn from the patient and introduced into the separation component 10 where the whole blood is separated to provide a target cell population. In a preferred embodiment in accordance with the present disclosure, the target cell population may be mononuclear cells. Other components separated from the whole blood, such as red blood cells and platelets may be returned to the patient or collected in pre-attached containers of the blood processing set.

The separated target cell population, e.g., mononuclear cells, is then prepared for treatment and irradiation in treatment component 20. As discussed above, in accordance with the present disclosure, treatment of mononuclear cells involves the photoactivation of a photoactive agent that has been combined with the mononuclear cells. Once treated, the mononuclear cells may optionally be provided to a washing component, which, as shown in FIG. 1, is housed within separation component 10. The treated mononuclear cells are separated from the supernatant and the concentrated cells may be returned to the patient. The supernatant liquid will typically include excess and unbound photoactivation agent. Optionally, the concentrated cells may further be combined with a suitable wash solution within separation/washing component 10. If washing of the treated mononuclear cells is performed, the suspension of mononuclear cells in a wash solution is then subjected to a centrifugal field (or other environment which can effect separation of the fluid components), whereby the mononuclear cells are concentrated and separated from the supernatant, including any remaining unbound photoactivation agent. Supernatant may then be diverted to an appropriate waste container, while the treated mononuclear cells are returned to the patient, as generally shown in FIG. 1.

Figure 2:
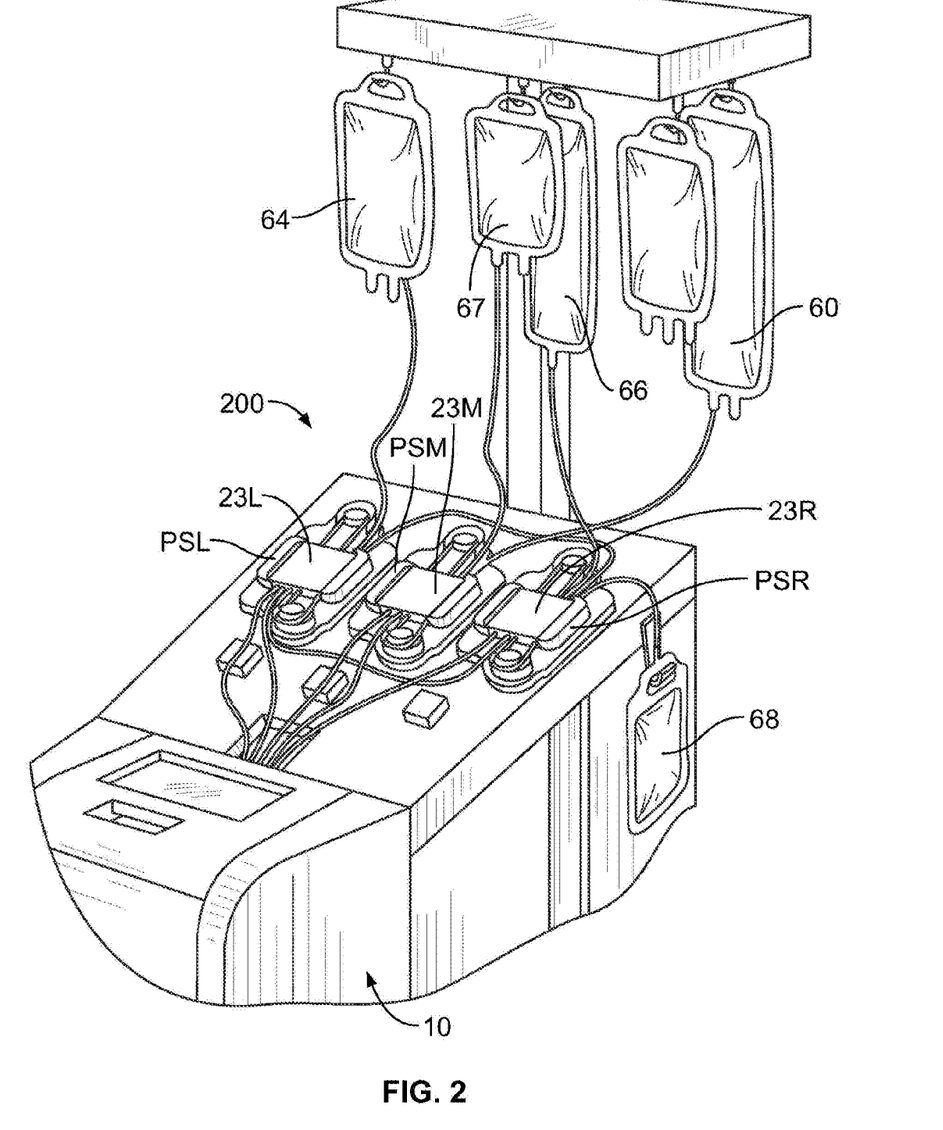
FIG. 2 is a partial perspective view of a multifunctional apheresis separator, according to an exemplary embodiment.
Figure 3:
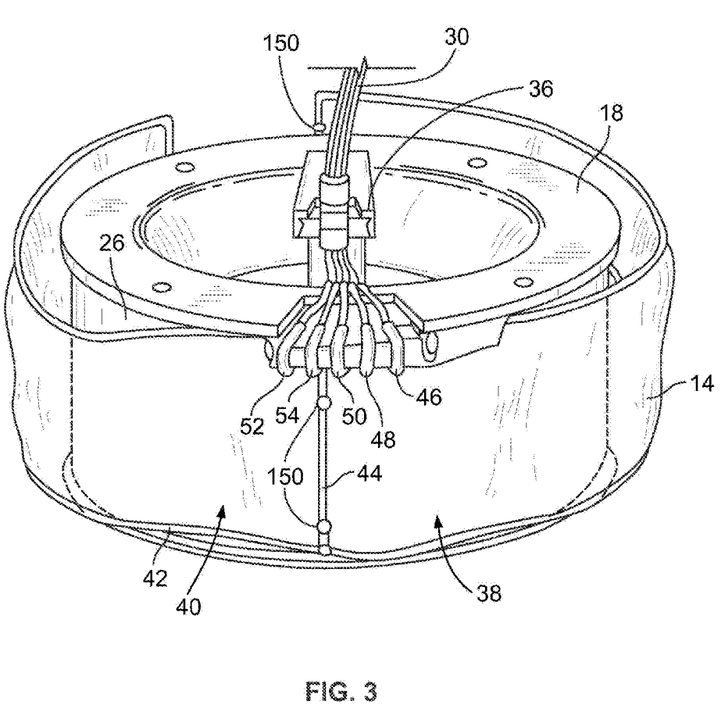
FIG. 3 is a perspective view of a separation chamber of the processing set used with the separator of FIG. 2, according to an exemplary embodiment.

Apparatus useful in the collection (and washing) of mononuclear cells, and providing the separation component 10 of FIG. 1, include the Amicus® Separator made and sold by Fenwal, Inc., of Lake Zurich, Ill. Mononuclear cell collections using a device such as the Amicus® are described in greater detail in U.S. Pat. No. 6,027,657, the contents of which is incorporated by reference herein in its entirety. Briefly, FIGS. 2-4 show a representative blood centrifuge 10 with fluid circuit 200 mounted thereon (FIG. 2), the fluid circuit (FIG. 4) having a blood processing container 14 (see FIG. 3) defining a separation chamber suitable for harvesting mononuclear cells (MNC) from whole blood. As shown in FIG. 2, a disposable processing set or fluid circuit 200 (which includes container 14) is mounted on the front panel of centrifuge 10. The processing set (fluid circuit 200) includes a plurality of processing fluid flow cassettes 23L, 23M and 23R with tubing loops for association with peristaltic pumps on device 10. Fluid circuit 200 also includes a network of tubing and pre-connected containers for establishing flow communication with the patient and for processing and collecting fluids and blood and blood components, as shown in greater detail in FIG. 4.

As seen in FIGS. 2 and 4, disposable processing set 200 may include a container 60 for supplying anticoagulant, a waste container 62 for collecting waste from one or more steps in the process for treating and washing mononuclear cells, a container 64 for holding saline or other wash or resuspension medium, a container 66 for collecting plasma, a container 68 for collecting the mononuclear cells and, optionally, container 69 for holding the photoactivation agent.

Container 68 may also serve as the illumination container, and is preferably pre-attached to with the disposable set 200. Alternatively, container 68 may be attached to set 200 by known sterile connection techniques, such as sterile docking or the like. With reference to FIG. 4, fluid circuit includes inlet line 72, an anticoagulant (AC) line 74 for delivering AC from container 60, an RBC line 76 for conveying red blood cells from chamber 12 of container 14 to container 67, a platelet-poor plasma (PPP) line 78 for conveying PPP to container 66 and line 80 for conveying mononuclear cells to and from separation chamber 14 and collection/illumination container 68. The blood processing set includes one or more venipuncture needle(s) for accessing the circulatory system of the patient. As shown in FIG. 4, fluid circuit 200 includes inlet needle 70 and return needle 82. In an alternative embodiment, a single needle can serve as both the inlet and outlet needle.

Fluid flow through fluid circuit 200 is preferably driven, controlled and adjusted by a microprocessor-based controller in cooperation with the valves, pumps, weight scales and sensors of device 10 and fluid circuit 200, the details of which are described in the previously mentioned U.S. Pat. No. 6,027,657.

The fluid circuit is further adapted for association with the treatment component (i.e., irradiation device) 20. Apparatus for the irradiation of the mononuclear cells are also known and are available from sources such as Cerus Corporation, of Concord, Calif. One example of a suitable irradiation device is described in U.S. Pat. No. 7,433,030, the contents of which is likewise incorporated by reference herein in its entirety. As shown and described in U.S. Pat. No. 7,433,030, irradiation device preferably includes a tray or other holder for receiving one or more containers during treatment. Other irradiation devices may also be suitable for use with the method and system described herein, including devices available from Macopharma and/or Vilber Lourmet.

As noted above, separation chamber 12 is defined by the walls of a flexible processing container 14 carried within an annular gap defined by a rotating spool element 18 and an outer bowl element (not shown). The processing container 14 takes the form of an elongated tube which is wrapped about the spool element 18 before use. The bowl and spool element 18 are pivoted on a yoke between an upright position and a suspended position, also not shown. In operation, the centrifuge 10 rotates the suspended bowl and spool element 18 about an axis 28, creating a centrifugal field within the processing chamber of container 14. Details of the mechanism for causing relative movement of the spool 18 and bowl elements as just described are disclosed in U.S. Pat. No. 5,360,542 entitled "Centrifuge with Separable Bowl and Spool Elements Providing Access to the Separation Chamber," which is also incorporated herein by reference.

Figure 5:
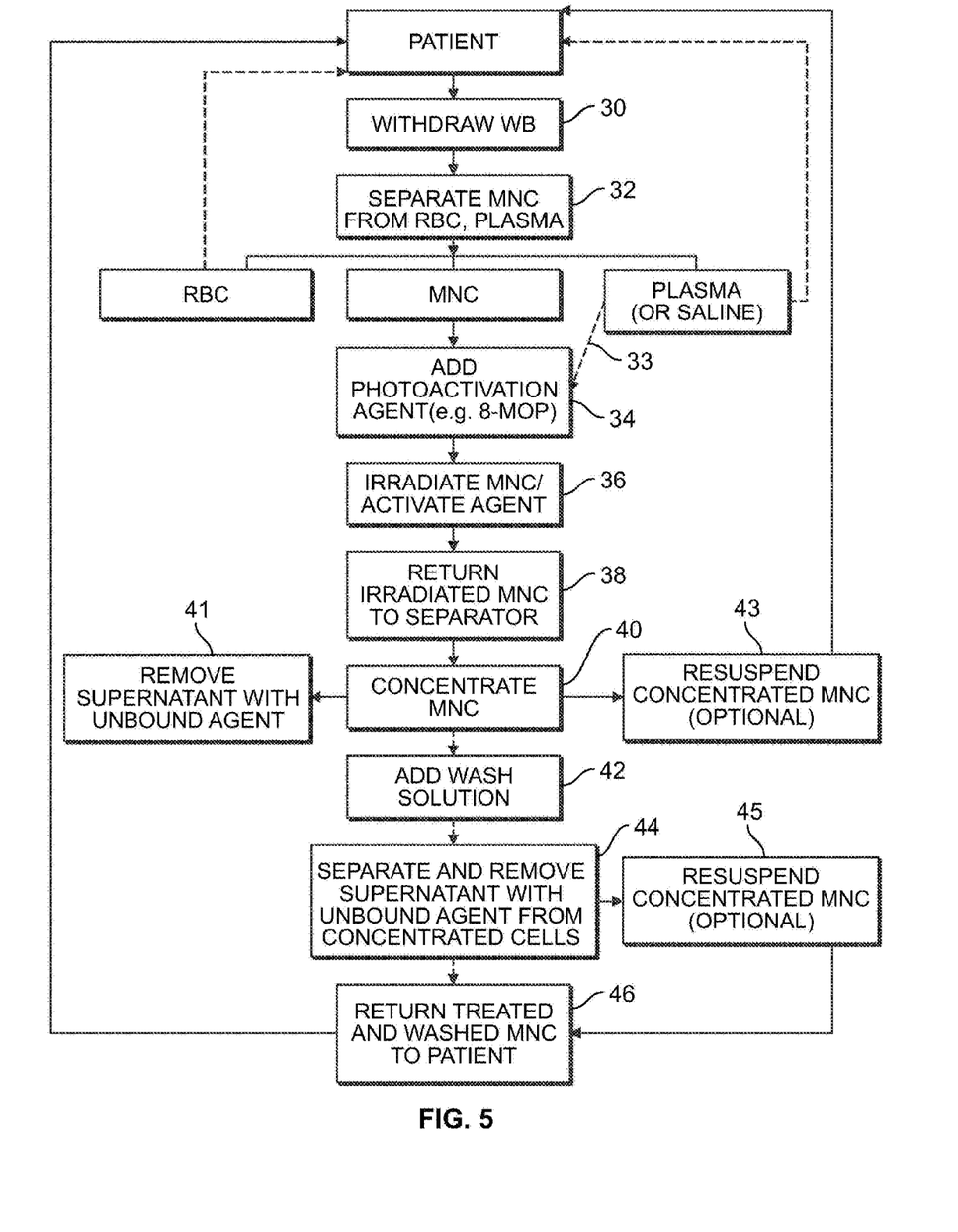
FIG. 5 is a flow chart setting forth the steps of the method of a photopheresis treatment, according to an exemplary embodiment.

With reference to FIG. 5, a representative method of treating mononuclear cells is seen. First, whole blood is withdrawn from a patient (step 30) through inlet needle 70 and introduced into the separation chamber 12 of container 14 of processing set 200, where the whole blood is subjected to a centrifugal field. The centrifugal field separates the target cell population, i.e., mononuclear cells, from red blood cells, platelets and plasma (step 32). The components such as red blood cells and platelets may be returned to the patient or may be diverted to a container (e.g., container 67) for further processing. Collection of the mononuclear cells may proceed in one or more cycles, with the number of processing cycles conducted in a given therapeutic procedure depending upon the total volume of MNC to be collected.

Effective treatment of the mononuclear cells with light may require that the collected mononuclear cells are provided in a suspension having a suitable hematocrit. Specifically, and as discussed in greater detail below, the level of hematocrit of the MNC suspension to be treated affects the amount of UV light received by the MNCs, as the red blood cells in the MNC suspension will block at least a portion the UV light from reaching the targeted MNCs. Precise control of hematocrit may be difficult to achieve, particularly with systems in which hematocrit sensors are used for this purpose. If the hematocrit of the suspended MNCs is too high (such that the red blood cells will interfere with the absorption of light by the MNCs), it may be desired or even necessary to dilute the mononuclear cells with a diluting solution, such as plasma or saline, as shown in step 33, to control the hematocrit so that a desired amount of UV light will reach the targeted MNC. The diluted mononuclear cells (in container 68) are then combined with the suitable photoactivation agent in step 34. Alternatively, the desired volume of the agent may be pre-added to the container.

As noted above, the mononuclear cells collected in accordance with the mononuclear cell collection process described above may be collected in container 68 that is suitable for irradiation by light of a selected wavelength. By "suitable for irradiation" it is meant that the walls of the container are sufficiently transparent to light of the selected wavelength to activate the photoactive agent. In treatments using UVA light, for example, container walls made of ethylene vinyl acetate (EVA) are suitable. Accordingly, container 68 in which the mononuclear cells are collected may serve both as the collection container and the irradiation container. Container 68 may be placed inside irradiation device 20 by the operator or, more preferably, may be placed inside the irradiation chamber of irradiation device 20 at the beginning of the ECP procedure and prior to whole blood withdrawal (as shown by the broken lines representing device 20 in FIG. 4). In any event, container 68 preferably remains integrally connected to the remainder of fluid circuit 200 during the entire procedure, thereby maintaining the closed or functionally closed condition of fluid circuit 200. In an alternative embodiment, the irradiation/illumination container may be a separate component disconnected from the fluid circuit 200. In such a case, a collection container that is part of the fluid circuit 200 may collect the mononuclear cells that are subsequently fed into an irradiation/illumination container within the irradiation device 20. Such an embodiment may be common in an offline system in which the collection container is disconnected from the fluid circuit 200 after collection and subsequently moved to the location of the irradiation device in an offline process. In both online and offline processes, the irradiation/illumination container may be configured to be wholly within the irradiation chamber such that the entire target cell population is within the irradiation chamber and irradiated simultaneously, or the irradiation/illumination container may be configured to feed only a portion of the target cell population at a time into the irradiation chamber, such as the configuration of the Therakos devices.

Automated control of the MNC collection and the irradiation treatment may be effected by the microprocessor-based controller of the respective separation device 10 and irradiation device 20 with some operator input for each device. Alternatively, operation of both separation device 10 and irradiation device 20 and the process steps carried out by each may be remotely controlled by a separate controller (e.g., a computer) that communicates with both.

The mononuclear cells with photoactivation agent (8-MOP) are then irradiated for a selected period of time (step 36). In one non-limiting example, during treatment, the mononuclear cell product may be exposed to UV bulbs having a wavelength in the UVA range of about 320 nm to 400 nm for a selected period of time, such as approximately 10-60 minutes, resulting in an average UVA exposure of approximately 0.5-5.0 $J/cm^2$ and use preferably approximately 1-2 $J/cm^2$ or even more preferably approximately 1.5 $J/cm^2$.

Once treatment is complete, the treated mononuclear cells may be returned to separator 10 (and more specifically, the separation chamber 12 of container 14) as shown in step 38 of FIG. 5. Once inside chamber 12, the MNC may be concentrated (step 40) to allow for the concentrated cells to have a smaller total volume as compared to un-concentrated cells. As a result, a smaller volume of concentrated MNCs may be reinfused to a patient faster. The concentrated cells may be resuspended in a suitable resuspension medium (e.g., plasma, saline) as shown in step 43 and returned to the patient. Optionally, prior to return to the patient, the concentrated and treated cells may be combined with a suitable wash solution (step 42), supplied (by the pumping action of pumps associated with cassette 23R) from containers 66 and/or 64 (see FIG. 4) is added to the concentrated cells.

In a method according to the present disclosure, a target light dose may first be determined by generating a standard curve relating light dose delivered to desired therapeutic response. Then, a light attenuation curve may be generated relating concentration of the light attenuating material to percent light absorbed by the attenuating material. The parameters of the product intended for treatment are targeted to a substantially flat portion of the light attenuation curve (i.e., where the percentage of light absorbed is not as sensitive to the product parameters). As a result, a selected fixed light dose is emitted which will deliver approximately the target light dose even with variations in the product parameters, meaning that precise control of the parameter is not required.

As one example, in photopheresis therapy, target cells such as mononuclear cells (MNCs) are combined with a psoralen (such as 8-MOP) and irradiated with UV light (specifically UV-A light). The UV light crosslinks 8-MOP to DNA strands inside the cell and on the cell wall, eventually causing apoptosis of the treated cells. As part of the collection procedure, the MNC product treated during photopheresis contains some amount of red blood cells and plasma, both of which absorb UV light, thereby preventing some portion of the UV light from being delivered to the desired target cells (e.g., MNC). As a result, the UV dose emitted from the UV source(s) is not equal to the UV dose delivered to the MNC.

Figure 6:
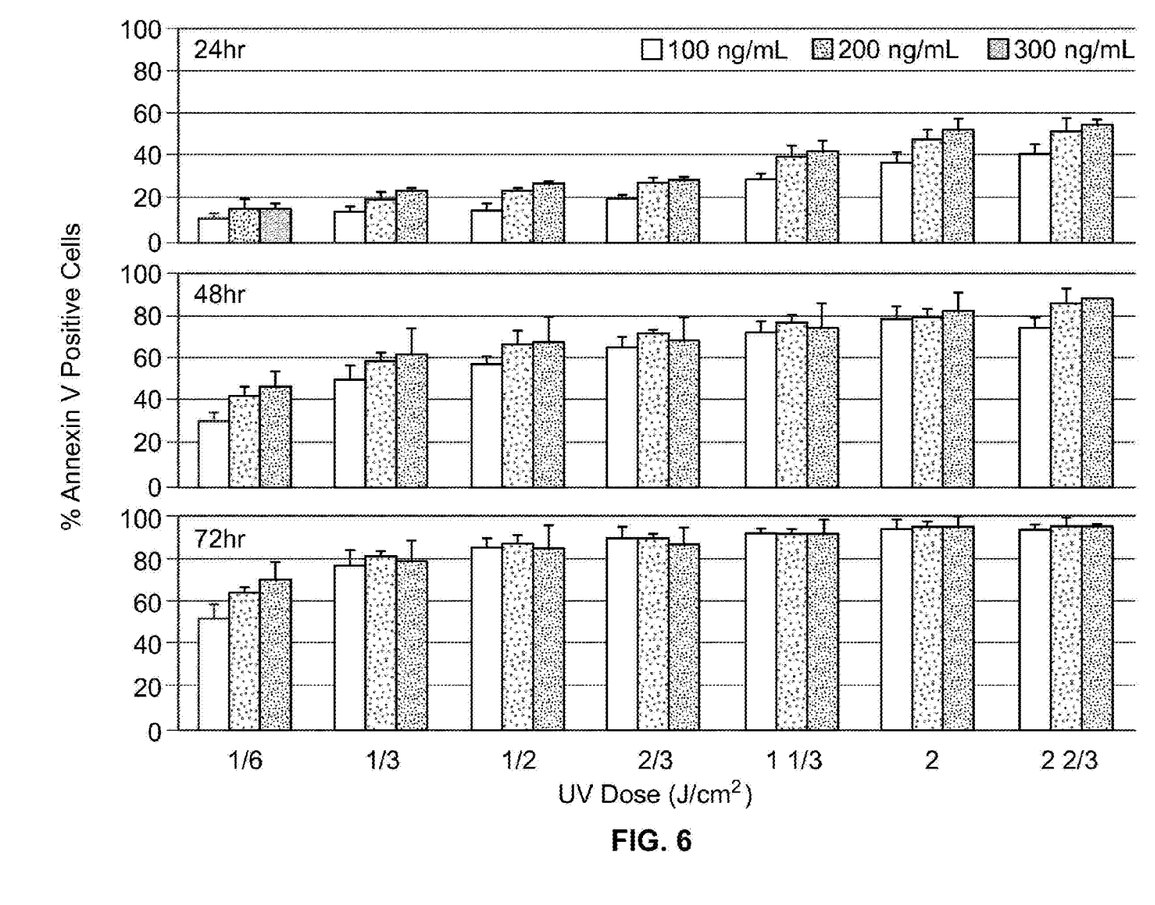
FIG. 6 is a series of three bar charts showing the degree of therapeutic response (the % of Annexin V Positive Cells) for varying light energy doses (in $J/cm^2$) and different amounts of light activatable compound (8-MOP at 100 ng/ml, 200 ng/ml and 300 ng/ml) at 24 hours, 48 hours and 72 hours, according to an exemplary embodiment.

To address this, a standard curve (delivered UV dose vs. lymphocyte apoptosis) can be generated by applying known UV doses to MNCs in the absence of RBC and plasma (which comprise the light attenuating material), and monitoring the apoptotic response in the lymphocytes after certain time points in culture, as discussed further below in connection with FIG. 6.

A second standard curve can be generated relating the hematocrit (which corresponds to the concentration of light attenuating material) to the percentage of light absorbed (=(1−(delivered÷emitted))×100%), as discussed below in connection with FIG. 7. From this curve, the product parameters for the procedure can be chosen from an area of the curve that is substantially flat (i.e., has a slope value closer to zero) such that the parameters of the product (hematocrit and volume, the latter corresponding to the product thickness) can vary slightly without significant impact on the UV light dose delivered to the MNC. The light dose vs. desired therapeutic response curve can be generated at varying 8-MOP concentrations and/or at multiple time points in culture (24, 48, 72 hours).

Example

A. Correlating Delivered Light Dose to Therapeutic Response

The creation of a standard curve relating light dose (UVA in this case) delivered to an apoptotic response in the lymphocytes (desired therapeutic result) for a suspension containing essentially no light attenuating material was determined as set forth below.

Apheresis-derived mononuclear cells from healthy donors were processed using a Ficoll-Paque gradient to produce a purified MNC population. The MNCs were then resuspended at $5\times10^6$ or $50\times10^6$ leukocytes/mL in RPMI 1640 media with 2 mM glutamine. The MNCs were transferred to 60 mm polystyrene culture dishes (5 mL cells/dish) and incubated with 100, 200, or 300 ng/mL of 8-MOP for 15 minutes in the dark. Irradiation was performed using an LED array capable of light intensities of 11.6±0.2 $mW/cm^2$ in the UVA band at 365±10 nm. After irradiation, MNCs were washed with RPMI 1640 media and resuspended at $1-2\times10^6$/mL in RPMI 1640 media with 2 mM glutamine and 10% human serum. Cells were cultured at 37° C. in a humidified chamber with 5% $CO_2$ for up to 72 hours. After 24, 48 and 72 hours, samples were assayed for apoptosis. Lymphocyte apoptosis was measured as the percentage of CD45+/Annexin-V positive cells in the lymphocyte forward/side scatter gate. Samples were repeated for at least n=3 at each UV dose/8-MOP concentration. Bar charts relating the percentage of Annexin-V positive cells at 24, 48 and 72 hours for various UV doses are seen in FIG. 6.

Example

B. Correlating Light Dose Absorbed to Amount of Attenuating Material

Then, a standard curve was generated relating hematocrit (i.e., the concentration of light attenuating material) and thickness of the product to the percentage of UV light absorbed (light absorbed by the light attenuating material) was determined as set forth below.

Apheresis-derived mononuclear cells (MNCs) from healthy donors were processed using a Ficoll-Paque gradient to produce a purified MNC population. Cells were resuspended at $10\times10^6$ leukocytes/mL in RPMI 1640 media with 2 mM glutamine. Red blood cells (the light attenuating material) were added to achieve 1, 2 or 3% hematocrit followed by incubation with 200 ng/ml of 8-MOP for 15 minutes in the dark. Cells were transferred to 60 mm polystyrene culture dishes at 2.83, 5.65, and 8.48 mL cells/dish to achieve product thicknesses of 1 mm, 2 mm, 3 mm, 4 mm (the sum of 1 mm plus 3 mm), and 5 mm (the sum of 2 mm plus 3 mm). Irradiation was performed using a commercially available UVA light box (Cerus). After irradiation, cells were again processed using a Ficoll-Paque gradient to produce purified MNCs. Final wash was performed with RPMI 1640 media and cells were resuspended at $1-2\times10^6$/mL in RPMI 1640 media with 2 mM glutamine and 10% human serum. Cells were cultured at 37° C. in a humidified chamber with 5% $CO_2$ for up to 72 hours. After 24, 48 and 72 hours, samples were assayed for apoptosis. Lymphocyte apoptosis was measured as the percentage of CD45+/Annexin-V positive cells in the lymphocyte forward/side scatter gate. Samples were repeated for at least n=3 at each hematocrit/thickness combination. UV dose delivered in each sample was determined from reading the bar charts of FIG. 6 based on apoptotic response. The percentage of UV absorbed by the light attenuating material was calculated as =[1−(UV delivered÷UV emitted)]×100%, and this percentage was plotted against the hematocrit of the samples at the various product thicknesses to generate a graph as seen in FIG. 7.

Figure 7:
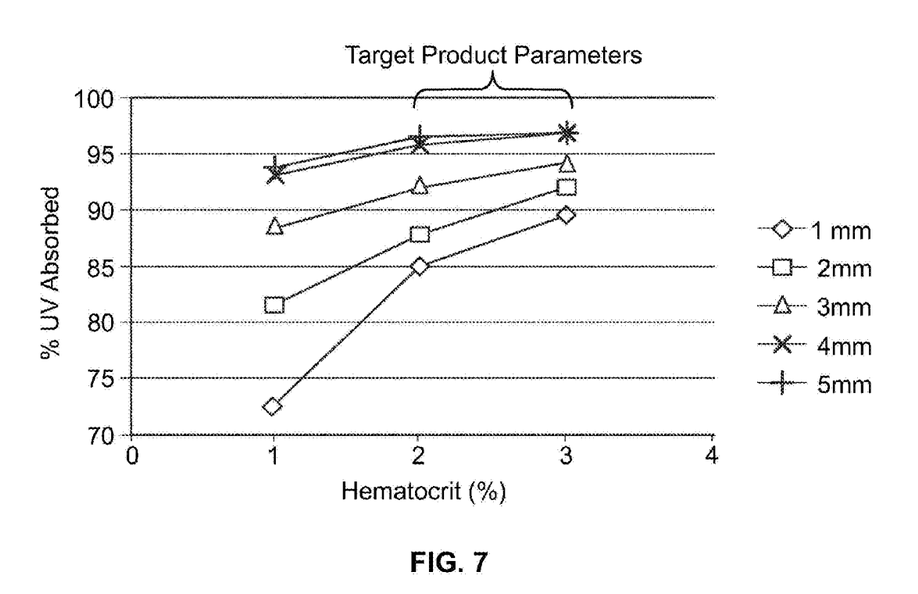
FIG. 7 is a plot of the % of light energy (UV) absorbed by a sample vs. the amount of light attenuating matter in the sample (% HCT) for various sample thicknesses (1 mm, 2 mm, 3 mm, 4 mm, and 5 mm), according to an exemplary embodiment.

With reference to FIG. 7, the plots for the samples having a thickness of 4 mm and 5 mm is substantially flat for suspensions having a HCT of from 2 to 3%. Thus, target product parameters according to the present method would be to prepare a suspension having approximately 2.5% HCT with a thickness of approximately 4.5 mm, while appreciating that the actual product hematocrit could vary from 2-3%, and the thickness could vary from 4-5 mm, without a significant impact on the UV dose delivered to the MNC, thereby still achieving the desired therapeutic response. In practice, the hematocrit for the MNC suspension is preferably designed into the apheresis procedure by which the MNC is collected, while the thickness of the suspension to be treated is controlled by knowing the surface area of the UV treatment container and the volume of the MNC suspension pumped into the container.

Thus, systems and methods have been disclosed for preparing a suspension to be subjected to light energy that includes light attenuating matter such that a desired dose is received and the desired therapeutic effect obtained. While the method has been described in the context of the extracorporeal photopheresis of mononuclear cells, it is not limited to the same, as other light dose cell treatment protocols could also utilize this method (i.e., pathogen inactivation).

Accuracy in calculation in irradiation treatment dosage may be further enhanced by the ability to account for variability in light intensities emitted by the irradiation source. Light sensors in the irradiation device 20 may be used to ensure in real-time that the proper dose of light is emitted to result in the desired apoptotic response of the target cell population. The dose of light emitted is a function of the intensity of the light emitted by light source as well as the period of time the light is emitted. A method available in the art for determining the amount of time to irradiate involves a calculation based on the amount of light attenuating matter (e.g., Hct) within the target cell suspension, thickness of the target cell suspension, and expected irradiation intensity based on the life expectancy and age of the irradiation source (e.g., UVA bulbs, LED lights). In the case in which the irradiation source is a bank of UVA bulbs, a UVA bulb life table (intensity versus bulb life) is determined experimentally and programmed into the system's memory. This method may not account for an instance in which one of the bulbs in the system does not follow the expected intensity versus bulb life pattern. Additionally, if one of the bulbs burns out or malfunctions, it is common for the system to be programmed to detect a change in current and require the whole bank of bulbs to be replaced before proceeding.

Figure 8:
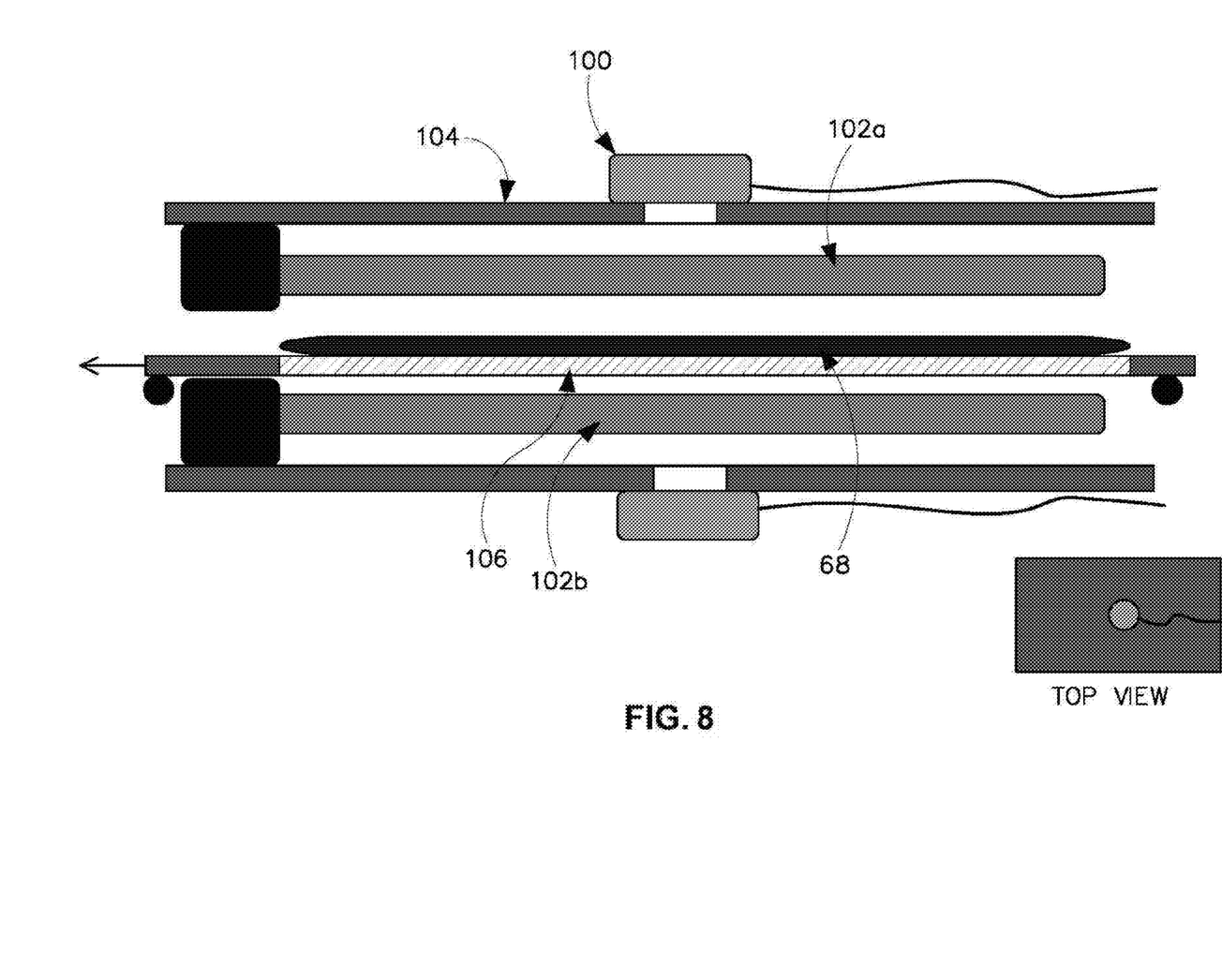
FIG. 8 is a diagram of a device for measuring the intensity of an irradiation source, according to an exemplary embodiment.

The use of light sensors to measure actual intensity rather than a light source expected life table may more accurately control the light dose emitted to the target cell population as well as allow for continuation of the photopheresis procedure even with a non-functional light bulb. The aforementioned U.S. Pat. No. 7,433,030 discloses one type of UVA sensor, although any suitable sensor may be used. FIG. 8 illustrates an exemplary embodiment of another type of sensor that may be used to measure actual intensity of UVA light. The UV-A sensor 100 may be mounted above an upper bank 102a of a plurality of UV-A light bulbs in an irradiation device, as shown in FIG. 8. A reflector plate 104 may be disposed above the upper bank 102 of light bulbs to reflect light emitted by the bulbs. An exposure plane 106 comprised of UV-transparent material may be disposed below the upper bank 102 of light bulbs to support illumination container 68. A lower bank 102b of a plurality of UV-A light bulbs may be disposed below the exposure plane 106. A second reflector plate 104 may be disposed below the lower bank 102b of light bulbs to reflect light emitted by the light bulbs. A second UV-A irradiation sensor 100 may optionally be mounted below the lower bank 102b of the light bulbs. The irradiation device may include any number of UV-A irradiation sensors 100, depending on the level of accuracy desired, and the UV-A irradiation sensors 100 may be tuned via filters to exclude frequencies of light other than the UV frequency light emitted from the irradiation source to minimize ambient light interference.

The light intensity observed by a UV-A sensor is dependent on the intensity of the UV-A light emitted by the UV-A light source, by the UV-A light reflected off of the internal surfaces of the irradiation chamber, and by the amount or percentage of UV-A absorbed by the target cell suspension, which may include both target and non-target cells as well as the suspension medium. Any number of UV-A sensors may be placed within the irradiation device, and a higher number of sensors may improve accuracy of intensity and absorption readings. If two or more UV-A sensors are utilized, the readings from the plurality of sensors may be averaged or be given different accuracy weightings.

Figure 9:
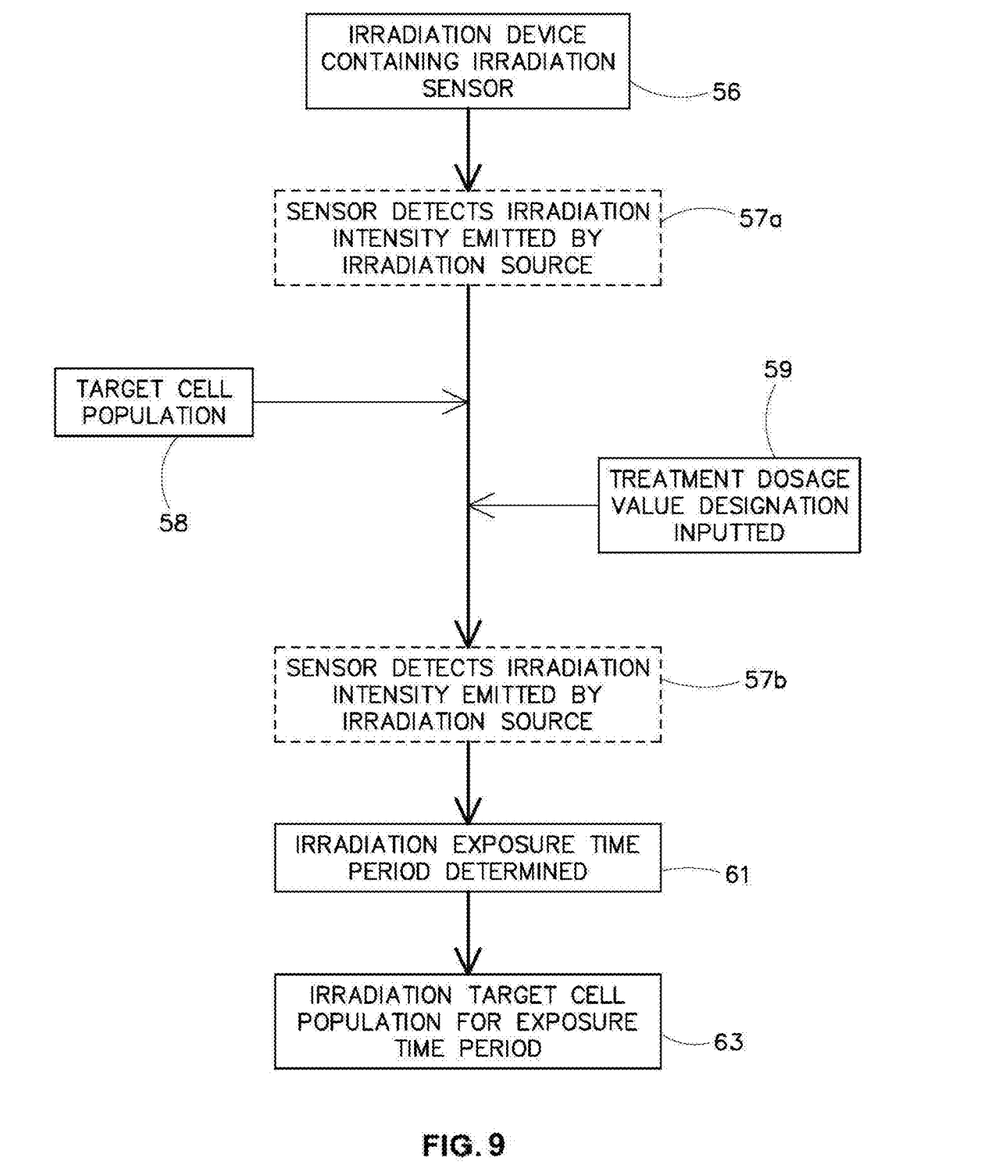
FIG. 9 is a flow chart illustrating a process for determining exposure time with light sensors, according to an exemplary embodiment.

FIG. 9 depicts a high-level portrayal of an illustrative method of determining exposure time with light sensors. An irradiation device containing an irradiation sensor is provided, as shown in step 56. The target cell population enters the irradiation device, as shown in step 58, and a desired treatment dosage value may be inputted into the processing circuit (step 59). Step 59 may be performed at any time prior to step 61 below. The UVA light intensity may be measured by the sensors before or after the target cell suspension is placed within the exposure chamber within the irradiation device. The UVA light intensity may be measured by the sensors after the target cell suspension is placed within the exposure chamber, as shown in step 57b, if the relationship between the UVA light intensity measured by the sensors with the target cell suspension in the exposure chamber vs without the target cell suspension in the exposure chamber is predetermined. If the UVA light intensity relationship with and without target cell suspension within the exposure chamber is unknown, the UVA light intensity may be measured by the sensors before the target cell suspension is placed within the exposure chamber, as shown in step 57a, in order to establish a baseline intensity. The UVA light intensity may also be measured and integrated over time throughout the procedure to provide more accurate control over UVA dose emitted as the UVA intensity emitted by the UVA bulbs may change during irradiation due to, for example, the temperature of the bulbs.

Irradiation exposure time period may be determined (step 61) based on the irradiation intensity of the irradiation source detected by the sensor (step 57a or 57b) and based on the desired treatment dosage value inputted in step 59. The target cell suspension may then be irradiated for the determined exposure time period, as shown in step 63.

Example

C. Determining Exposure Time with Light Sensors Detecting Intensity of Light Source With reference to FIG. 9, an illustrative method of determining exposure time with light sensors is shown. A MNC suspension having approximately 2.0% HCT with a thickness of approximately 4 mm may be prepared with 200 ng/mL of photoactivatable agent (e.g., step 58). If the apoptosis profile desired is 40% at 24 hours, 75% at 48 hours, and 90% at 72 hours, as is the case in this example, FIG. 6 indicates that the UV dose that should be delivered to the MNC population is 1⅓ J/cm$^2$ (approximately 1.33 J/cm$^2$). FIG. 7 indicates that at 2.0% HCT and a 4 mm thickness, approximately 96% of the light emitted is absorbed by the light attenuating material and approximately 4% of the light emitted is received by the target cell population, i.e., MNCs. It can then be calculated that the light emitted by the light source must be 33.33 J/cm$^2$ in order for a 4% totaling 1.33 J/cm$^2$ to be delivered to the target cells (e.g., step 59).

In Example A above, an LED bulb array with a light intensity of approximately 11.6 mW/cm$^2$ was utilized. The same LED bulb array with the same light intensity may be used in the current example. 11.6 mW/cm$^2$ may be converted to 0.0116 J/(cm$^2$×s). Since light emitted should be 33.33 J/cm$^2$, it can be calculated that the exposure time should be 33.33 J/cm$^2$÷0.0116 J/(cm$^2$×s)=48 minutes (e.g., step 61).

In an event in which one or more of the LED bulbs in the bulb array may malfunction and reduce the emitted light intensity to, for example, 8.0 mW/cm$^2$, the light sensors may detect the decreased light intensity and adjust the exposure time to reflect this decrease and continue the photopheresis procedure. In the example in which the light intensity has been reduced to 8.0 mW/cm$^2$ as measured by the light sensors (e.g., step 57a or 57b), it can be calculated that the exposure time should be 33.33 J/cm$^2$÷0.008 J/(cm$^2$×s)=69 minutes (e.g., step 61). The irradiation device may be programmed to reset or update the exposure time to the new calculation of 69 minutes (or some prorated value in between 48 and 69 minutes depending on the UVA light dose emitted prior to the decrease in bulb UVA intensity) and thereby maintain the light emitted to as close to 33.33 J/cm$^2$ as possible such that the target cell population is delivered the expected 1.33 J/cm$^2$. Updates to the exposure time may be done continuously (e.g., in real time) or over preselected periods of time (e.g., regular or random intervals), as shown in e.g., step 61.

The irradiation device 20 may be configured via a processing circuit such that when the emitted light intensity during irradiation as observed by the sensor changes in value, a response action may be performed. The response action may comprise, in addition to resetting the exposure time to the new calculation, the processing circuit terminating the procedure, notifying the operator of below- or above-threshold irradiation intensity, and/or notifying the operator to select a different exposure time. The processing circuit may comprise analog and/or digital electrical components configured or programmed to perform any of the functions described herein. The processing circuit may comprise one or more microprocessors, microcontrollers, application-specific integrated circuits, programmable logic devices, etc., which may further be programmed by way of an operating system, applications, and/or other computer programs stored on a tangible memory device. Memory may comprise RAM, Flash, volatile and/or non-volatile memory of a variety of types used to support processing circuit in executing its functionalities.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The invention claimed is:

1. A method for determining irradiation exposure time during an extracorporeal photopheresis procedure, comprising the steps of:
   providing an illumination container holding a target cell suspension containing a light attenuating material having a hematocrit value and a concentration of a photoactivation agent, wherein the illumination container holding the target cell suspension has a thickness value within a target thickness range of 4-5 mm;
   providing an irradiation device comprising 1) an exposure chamber configured to receive the illumination container holding the target cell suspension and the photoactivation agent, 2) an irradiation sensor configured to detect intensity of irradiation emitted by an irradiation source configured to irradiate contents within the illumination container for an exposure time period, and 3) a processing circuit in communication with the irradiation sensor;
   receiving via the processing circuit a first input of the concentration of the photoactivation agent;
   receiving via the processing circuit a second input from the irradiation sensor of the intensity of irradiation emitted by the irradiation source;
   calculating via the processing circuit the exposure time period based on the first input of the concentration of the photoactivation agent and the second input of the intensity of irradiation, to achieve a designated treatment dosage, wherein differing concentrations of the photoactivation agent yield differing exposure time periods, and wherein the exposure time period is calculated without taking into account the thickness value of the illumination container holding the target cell suspension; and
   irradiating the target cell suspension with the irradiation source for the exposure time period.

2. The method for determining irradiation exposure time of claim 1, wherein the target cells comprise mononuclear cells.

3. The method for determining irradiation exposure time of claim 1, wherein the photoactivation agent is 8-methoxypsoralen.

4. The method for determining irradiation exposure time of claim 1, wherein the irradiation source emits UV-A light and the irradiation sensor senses UV-A light.

5. The method for determining irradiation exposure time of claim 1, wherein the irradiation source comprises at least one of a light bulb and LED lighting.

6. The method for determining irradiation exposure time of claim 1, wherein a plurality of irradiation sensors is disposed within the irradiation device.

7. The method for determining irradiation exposure time of claim 6, wherein the processing circuit is configured to average differing irradiation intensity values detected by the plurality of irradiation sensors in determining the exposure time period.

8. The method for determining irradiation exposure time of claim 1, wherein the hematocrit value is in the range of 2-3%.

9. The method for determining irradiation exposure time of claim 1, wherein the processing circuit comprises one or more microprocessors, microcontrollers, application-specific integrated circuits, and/or programmable logic devices.

* * * * *